United States Patent
Haraguchi et al.

(10) Patent No.: US 12,285,300 B2
(45) Date of Patent: Apr. 29, 2025

(54) ARM DEVICE

(71) Applicant: RIVERFIELD INC., Tokyo (JP)

(72) Inventors: Daisuke Haraguchi, Tokyo (JP); Kotaro Tadano, Tokyo (JP); Noriaki Kanazawa, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 1215 days.

(21) Appl. No.: 17/042,678

(22) PCT Filed: Sep. 10, 2018

(86) PCT No.: PCT/JP2018/033438
§ 371 (c)(1),
(2) Date: Sep. 28, 2020

(87) PCT Pub. No.: WO2019/193775
PCT Pub. Date: Oct. 10, 2019

(65) Prior Publication Data
US 2021/0059783 A1    Mar. 4, 2021

(30) Foreign Application Priority Data

Apr. 6, 2018  (JP) .................................. 2018-073837

(51) Int. Cl.
*A61B 90/50*  (2016.01)
*A61B 1/00*   (2006.01)
(Continued)

(52) U.S. Cl.
CPC .......... *A61B 90/50* (2016.02); *A61B 1/00149* (2013.01); *A61B 17/00234* (2013.01);
(Continued)

(58) Field of Classification Search
CPC ............... A61B 90/50; A61B 1/00149; A61B 17/00234; A61B 2017/00544;
(Continued)

(56) References Cited

U.S. PATENT DOCUMENTS 3,887,267 A * 6/1975 Heller .................... F16M 11/18
                                                           359/384
5,397,323 A   3/1995 Taylor et al.
(Continued)

FOREIGN PATENT DOCUMENTS

JP   H0313113 U   2/1991
JP   H06261911 A  9/1994
(Continued)

OTHER PUBLICATIONS

International Search Report (Form PCT/ISA210) for International Application No. PCT/JP2018/033438, mailed Nov. 13, 2018 (5 pages including English translation).
(Continued)

*Primary Examiner* — Jonathan T Kuo
*Assistant Examiner* — Vynn V Huh
(74) *Attorney, Agent, or Firm* — Withrow + Terranova, PLLC; Vincent K. Gustafson

(57) ABSTRACT

Provided is an arm device. The arm device includes: a first gimbal portion configured to rotatably support an instrument about a first rotational axis extending along an axis line of the instrument; a second gimbal portion configured to rotate the instrument about a second rotational axis extending along a direction intersecting the first rotational axis; a distal portion configured to rotate the instrument about a third rotational axis extending to intersect a plane including the first rotational axis and the second rotational axis. The third rotational axis has an inclination angle greater than 0 degree and less than 90 degrees when a horizontal direction is defined as 0 degree and an upper vertical direction is defined as 90 degrees.

8 Claims, 10 Drawing Sheets

(51) Int. Cl.
*A61B 17/00* (2006.01)
*A61B 34/30* (2016.01)
(52) U.S. Cl.
CPC ............... *A61B 2017/00544* (2013.01); *A61B 2034/301* (2016.02); *A61B 2090/504* (2016.02); *A61B 2090/506* (2016.02)
(58) Field of Classification Search
CPC ........ A61B 2034/301; A61B 2090/504; A61B 2090/506; A61B 2034/302; A61B 34/30–37; B25J 13/00–089
See application file for complete search history.

(56) References Cited

U.S. PATENT DOCUMENTS

| | | | | |
|---|---|---|---|---|
| 5,828,197 | A * | 10/1998 | Martin | A61B 34/76 318/560 |
| 2005/0129495 | A1 * | 6/2005 | Brogardh | B25J 9/0072 414/680 |
| 2006/0245894 | A1 * | 11/2006 | Merz | B25J 9/104 414/680 |
| 2006/0264915 | A1 | 11/2006 | Jensen | |
| 2009/0283647 | A1 * | 11/2009 | Yasunaga | A61B 90/50 248/123.2 |
| 2016/0365771 | A1 | 12/2016 | Kokubo et al. | |

FOREIGN PATENT DOCUMENTS

| | | | | |
|---|---|---|---|---|
| JP | H08224246 | A | 9/1996 | |
| JP | 2003053684 | * | 2/2003 | |
| JP | 2003053684 | A | 2/2003 | |
| JP | 3579379 | B2 | 10/2004 | |
| JP | 2018051711 | A | 4/2018 | |
| WO | 2015133291 | A1 | 9/2015 | |
| WO | WO-2017210073 | A1 * | 12/2017 | ............. A61B 34/25 |

OTHER PUBLICATIONS

Written Opinion (Form PCT/ISA/237) for International Application No. PCT/JP2018/033438, mailed Nov. 13, 2018 (10 pages including partial English translation of Box V).

International Preliminary Report on Patentability for International Patent Application No. PCT/JP2018/033438, mailed Oct. 15, 2020, 9 pages.

Extended European Search Report for European Patent Application No. 18913303.6, mailed Nov. 5, 2021, 8 pages.

Notice of Reasons for Refusal for Japanese Patent Application No. 2018073837, mailed Jun. 23, 2020, 6 pages.

Decision to Grant for Japanese Patent Application No. 2018073837, mailed Jul. 28, 2020, 4 pages.

* cited by examiner

ARM DEVICE

CROSS-REFERENCE TO RELATED APPLICATION(S)

This application is the U.S. national phase under 35 U.S.C. § 371 of International Application No. PCT/JP2018/033438 filed on Sep. 10, 2018, and further claims priority to Japanese Patent Application No. 2018-073837 filed on Apr. 6, 2018, wherein the entire contents of the foregoing applications are hereby incorporated by reference herein.

TECHNICAL FIELD

The present disclosure relates to an arm device, and particularly relates to an arm device suitable for endoscopic surgery and endoscopic examinations using an endoscope, and for general surgery.

BACKGROUND ART

Endoscopic surgery using an endoscope has been known. In the endoscopic surgery, an instrument holder to hold an instrument, such as an endoscope and a forceps. A known instrument holder is an instrument holder having a gimbal portion and an arm portion and capable of operating an instrument three-dimensionally. The instrument holder is also capable of holding an instrument at any position. Also, in endoscopic examinations using an endoscope and, for example, general open abdominal surgery (hereinafter, endoscopic surgery, endoscopic examinations, and general surgery are also collectively referred to as "examinations and operations".), more and more examinations and procedures are being performed using such an instrument holder to hold an instrument.

Under this situation, it is known that, for example, an endoscope observation angle at which an endoscope is to be held during endoscopic surgery varies for each target disease, and each target disease has a suitable observation angle. Examples of the endoscope observation angle frequently used in endoscopic surgery are as below.

In digestive surgery, frequently used is an endoscope observation angle to hold an endoscope obliquely downward relative to a surgical bed. In respiratory surgery, frequently used is an endoscope observation angle to hold an endoscope in a substantially vertical attitude relative to a surgical bed. In urological surgery, frequently used is an endoscope observation angle to hold an endoscope in a substantially horizontal attitude relative to a surgical bed. Moreover, surgical tools for use with the endoscope are each held and used at an appropriate angle corresponding to the target disease and the endoscope observation angle.

In order to correspond to different endoscope observation angles as described above, regarding the instrument holder, for example, instrument holders with various configurations have been proposed (see, for example, Patent Documents 1 and 2).

PRIOR ART DOCUMENTS

Patent Documents

Patent Document 1: Japanese Patent No. 3579379
Patent Document 2: Japanese Unexamined Utility Model Application Publication No. H3-13113

SUMMARY OF THE INVENTION

Problems to be Solved by the Invention

The aforementioned gimbal portion has three rotational axes intersecting one another. The gimbal portion with this configuration may assume a specific attitude in which two rotational axes are located in the same direction plane depending on rotational positions of the three rotational axes. In the gimbal portion assuming the specific attitude, original three degrees of freedom will be reduced to two degrees of freedom. If the gimbal portion takes an attitude close to the specific attitude, it will be difficult to operate the instrument holder in a specific direction, and an operation range of the instrument will be narrowed.

In order to allow use of the instrument holder without difficulty in various endoscopic surgery, the gimbal portion is required not to take the specific attitude within a range of the endoscope observation angle. However, the technique disclosed in Patent Document 1 or 2 does not achieve a configuration in which the gimbal portion of the instrument holder can be avoided from assuming the specific attitude.

In the configuration disclosed in Patent Document 1, when a medical manipulator 1 is held in a substantially horizontal attitude, a rotational axis 106 overlaps a rotational axis 104. In this situation, the attitude of the gimbal portion is the specific attitude. In case of using the configuration disclosed in Patent Document 1 for endoscopic surgery in the urological surgery, operability might be impaired.

In this regard, if the configuration disclosed in the Patent Document 1 is arranged with a distal portion 15 (including the rotational axis 104) inclined by 90°, the gimbal portion can be avoided from assuming the specific attitude. Thus, when an instrument holder with the distal portion 15 inclined by 90° is used for endoscopic surgery in the urological surgery, operability might be improved.

In such case, however, when the medical manipulator 1 is held in a substantially vertical attitude, the gimbal portion might assume the specific attitude. Thus, there has been a problem that even if the instrument holder with the distal portion 15 inclined by 90° is used for endoscopic surgery in the respiratory surgery, operability might be impaired when the medical manipulator 1 is held in a substantially vertical attitude.

In a configuration disclosed in Patent Document 2, a microscope 12 retains a vertical attitude relative to a parallel link 15. In ophthalmic surgery, an observation angle at which the microscope 12 is held in a vertical attitude is suitable.

However, according to the configuration disclosed in Patent Document 2 using the parallel link 15, three rotational axes corresponding to front-rear, left-right, and rotation cannot be achieved. The observation angle of endoscopic surgery requires three rotational axes corresponding to front-rear, left-right, and rotation, and the configuration disclosed in Patent Document 2 provides insufficient degrees of freedom.

In one aspect of the present disclosure, it is desirable to provide an arm device that facilitates ensuring an operational range of an instrument to be used for endoscopic surgery, endoscopic examinations, general surgery, and so on.

Means for Solving the Problems

An arm device of the present disclosure comprises: a first gimbal portion configured to rotatably support an instrument about a first rotational axis extending along an axis line of the instrument; a second gimbal portion configured to rotate the instrument about a second rotational axis extending along a direction intersecting the first rotational axis; a distal portion configured to rotate the instrument about a third rotational axis extending to intersect a plane including the first rotational axis and the second rotational axis. The third rotational axis has an inclination angle greater than 0 degree and less than 90 degrees when a horizontal direction is defined as 0 degree and an upper vertical direction is defined as 90 degrees.

According to the arm device of the present disclosure, the third rotational axis has an inclination angle greater than 0 degree and less than 90 degrees, and thus, the first rotational axis and the third rotational axis will not have the same inclination angle during examinations and operations. In other words, the degrees of freedom of rotation of the supported instrument will not be reduced from three to two.

The third rotational axis preferably has an inclination angle of 45 degrees.

The third rotational axis having an inclination angle of 45 degrees leads to symmetric operability of the arm device when the axis line of the instrument is oriented horizontal or oriented vertical. Thus, an operation angle range of the instrument can be substantially maximum.

The distal portion is preferably supported by an arm portion that comprises at least one parallel link.

Supporting the distal portion by the arm portion that comprises the parallel link facilitates maintaining an attitude of the distal portion constant if an arrangement position of the distal portion is changed. In other words, the inclination angle of the third rotational axis can be easily maintained constant.

The arm device of the present disclosure preferably further comprises a link portion having one end relatively rotatably mounted on a support and the other end relatively rotatably mounted on the distal portion; and a drive portion configured to change a relative position of the distal portion with respect to the support, and to maintain the attitude of the distal portion constant.

Supporting the distal portion by the link portion and the drive portion in this manner facilitates maintaining the attitude of the distal portion constant if the arrangement position of the distal portion is changed. In other words, the inclination angle of the third rotational axis can be easily maintained constant.

The arm device of the present disclosure preferably further comprises an actuator configured to drive the parallel link to thereby move a position of the distal portion; and a gravity compensator configured to apply a force to move the distal portion upward on the parallel link.

The arm device with the actuator and the gravity compensator allows reduction in a driving force required for the actuator to move the position of the distal portion supporting the instrument. Thus, size reduction of the actuator can be facilitated.

For example, as compared with a counter-weight arm device provided with a counter weight that balances with a weight of a distal portion supporting an endoscope, size reduction of a rear part of the arm device located opposite to an extending direction of the instrument can be facilitated. Such size reduction of the rear part reduces interference, by the arm device, of operation by an operator, an assistant, or a nurse during examinations and operations.

The actuator is preferably an air pressure actuator configured to be driven by receiving air supply.

Use of an air pressure actuator for the actuator facilitates an increase in power-to-weight ratio, and allows achievement of simplified linear motion without using a deceleration mechanism. Accordingly, size reduction of the arm device can be further facilitated.

The distal portion is preferably supported by an arm portion that extends along a horizontal direction and is configured to rotate about a rotational axis line extending vertically.

By supporting the distal portion by the arm portion that extends along the horizontal direction and is configured to rotate about the rotational axis line extending vertically, it is facilitated to maintain the attitude of the distal portion if the arrangement position of the distal portion is changed. In other words, the inclination angle of the third rotational axis can be easily maintained constant.

The arm device of the present disclosure preferably further comprises a holding portion that is attachable to and detachable from a place where the instrument is to be arranged for use.

The arm device provided with a holding portion facilitates fixation of the arm device to a specified place. For example, fixation of the arm device to a surgical bed in endoscopic surgery is facilitated, and thus it can be facilitated to maintain the attitude of the distal portion constant when an operation, such as tilting the surgical bed for postural change of a patient, is performed. In other words, the inclination angle of the third rotational axis can be easily maintained constant.

Effects of the Invention

The arm device of the present disclosure achieves an effect of facilitating ensuring an operational range of an instrument during examinations and operations since the third rotational axis has an inclination angle greater than 0 degree and less than 90 degree.

Figure 1:
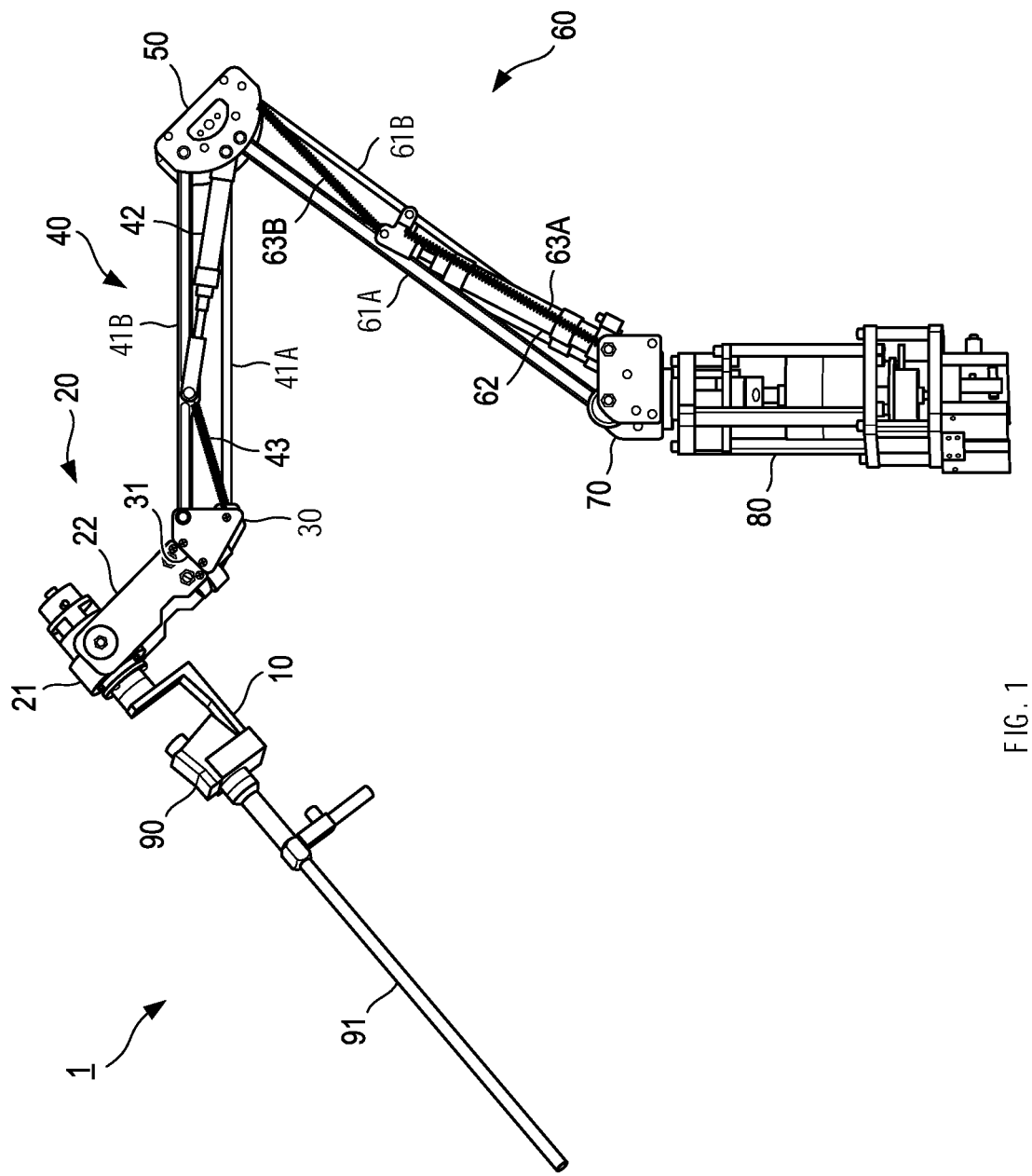
FIG. 1 is a view illustrating a configuration of an arm device of a first embodiment.

EXPLANATION OF REFERENCE NUMERALS 1, 201, 301, 401 . . . arm device; 21, 421 . . . first gimbal portion; 22, 422, 522 . . . second gimbal portion; 30 . . . distal portion; 40, 340 . . . first arm portion (arm portion); 42 . . . first air pressure actuator (air pressure actuator); 43 . . . first gravity compensator (gravity compensator); 60 . . . second arm portion (arm portion); 62 . . . second air pressure actuator (air pressure actuator); 63A, 63B . . . second gravity compensator (gravity compensator); 80 . . . holding portion; 90 . . . endoscope (instrument); 101 . . . first rotational axis; 102 . . . second rotational axis; 103 . . . third rotational axis; 241 . . . first link portion (link portion); 245 . . . first drive portion (drive portion); 261 . . . second link portion (link portion); 265 . . . second drive portion (drive portion); 900 . . . robot forceps

MODE FOR CARRYING OUT THE INVENTION

First Embodiment

Hereinafter, a description will be given of an arm device 1 of a first embodiment with reference to FIG. 1 to FIG. 6. In the first embodiment, the arm device 1 holds an endoscope 90 in endoscopic surgery. An instrument to be held by the arm device 1, other than an endoscope, may be a forceps; an energy device, such as an electric scalpel, a laser scalpel, and a hemostatic device; a surgical tool, such as a stapler, biopsy device, and scissors; a robot forceps, which are used in endoscopic surgery, endoscopic examination, and general surgery; and other instruments to be used in medical procedures. There is no limitation to the instrument. The aforementioned robot forceps comprises an elongated rod-shaped shaft, a forceps portion provided at a distal end of the shaft, and a main body portion provided at a proximal end of the shaft to drive the forceps portion and the shaft. In the robot forceps, if the shaft is rotatable about its axis line relative to the main body portion by a user's manipulation or driving from the main body portion, such configuration may be regarded as a configuration of "a first gimbal portion" in the present disclosure. In a case where the forceps portion and the shaft are separable from the main body portion in the robot forceps, the main body portion may be configured as a part of the arm device.

Figure 2:
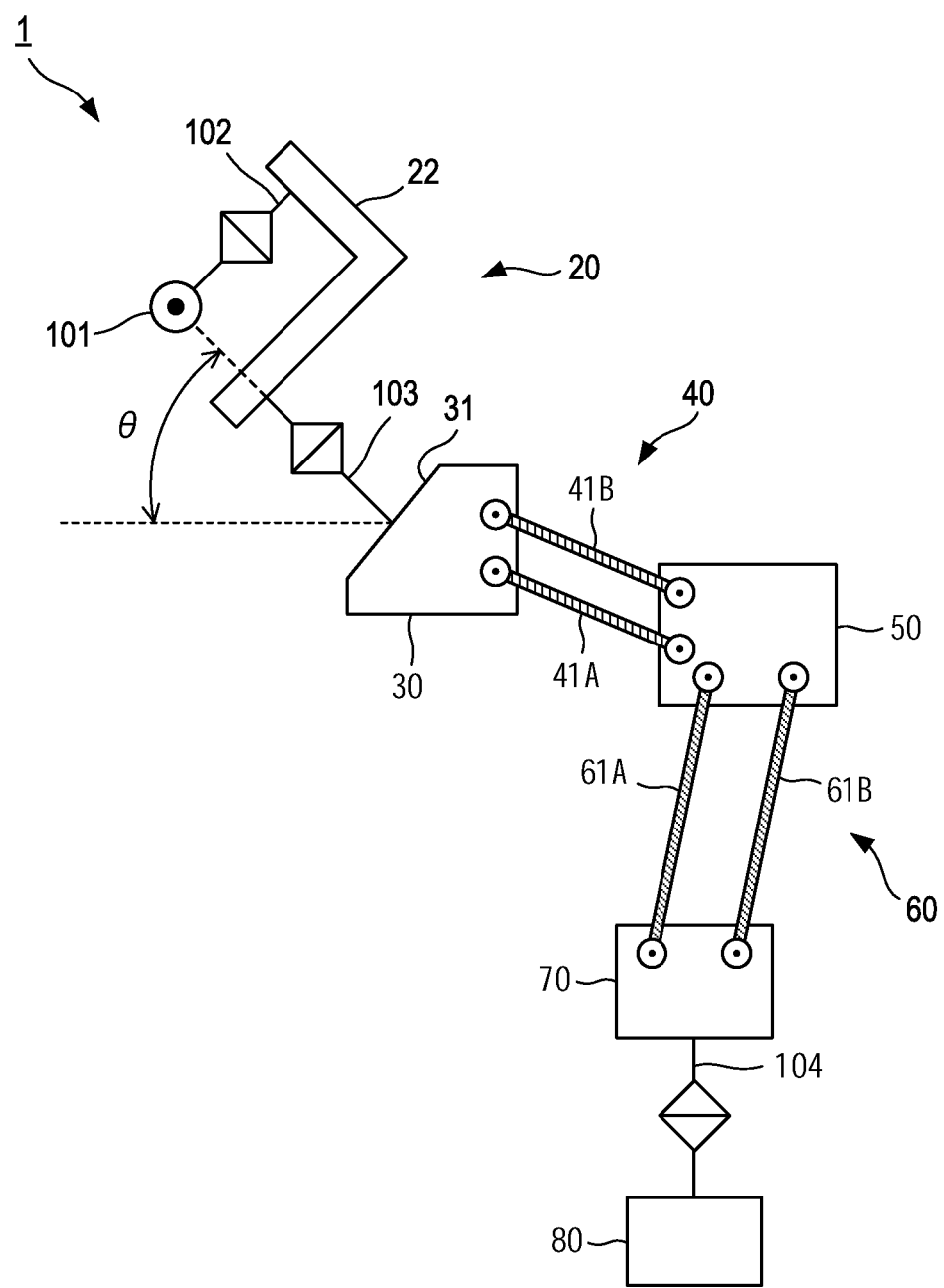
FIG. 2 is a schematic diagram illustrating the configuration of the arm device in FIG. 1.

As shown in FIG. 1 and FIG. 2, the arm device 1 comprises a holder 10 to hold the endoscope 90, a gimbal mechanism 20, a distal portion 30, a first arm portion (an arm portion) 40, a joint 50, a second arm portion (an arm portion) 60, a base 70, and a holding portion 80.

Figure 3:
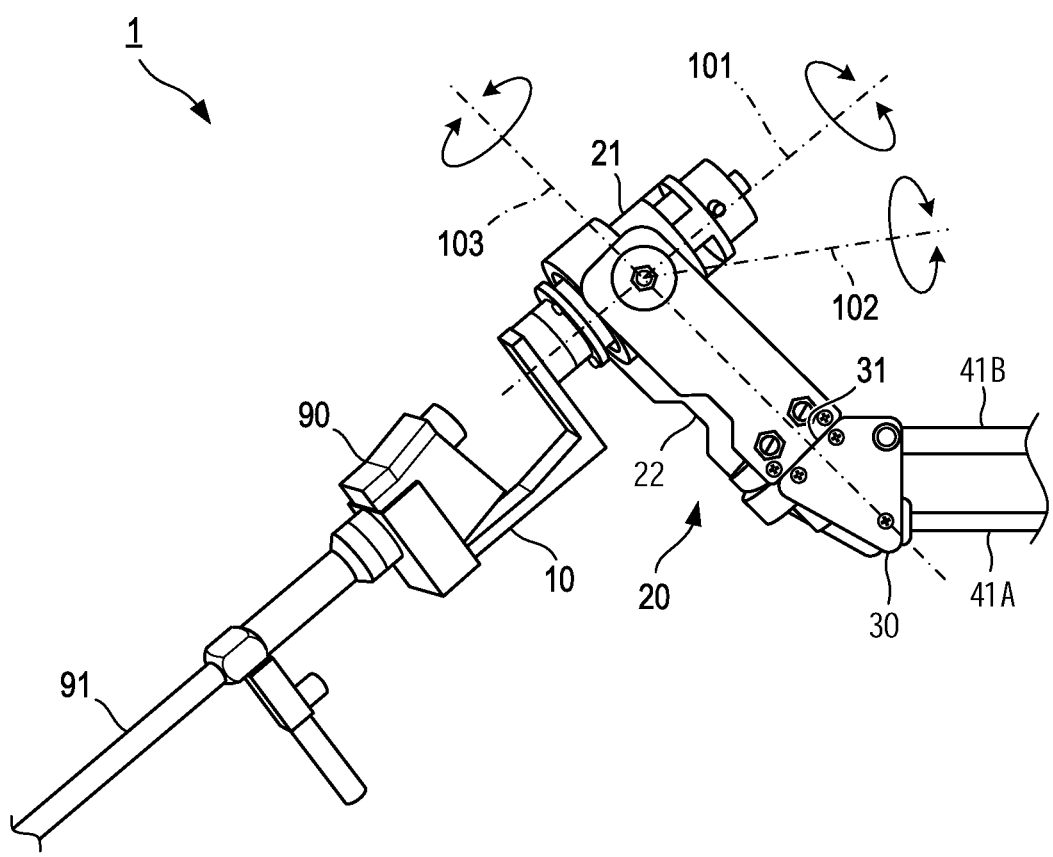
FIG. 3 is a partial enlarged view illustrating a configuration of a gimbal mechanism in FIG. 1.

As shown in FIG. 3, the holder 10 holds the endoscope 90 and is mounted on the first gimbal portion 21 of the gimbal mechanism 20. The holder 10 may have any configuration capable of holding the endoscope 90, and is not limited to any specific configuration.

The gimbal mechanism 20 comprises the first gimbal portion 21 and a second gimbal portion 22. The first gimbal portion 21 rotatably supports the endoscope 90 about a first rotational axis 101 extending along an axis line of the endoscope 90. The second gimbal portion 22 rotatably supports the endoscope 90 about a second rotational axis 102 extending along an intersecting direction (more preferably an orthogonal direction) with the first rotational axis 101.

The axis line of the endoscope 90 means an axis line of a viewing tube 91 having a tubular shape in the endoscope 90. In the first embodiment, a description will be given of an example in which the axis line of the endoscope 90 is the axis line of a viewing tube having a cylindrical or columnar shape.

The first rotational axis 101 that extends along the axis line of the endoscope 90 may suffice, and these may be coincident with each other or may be arranged apart from each other. In the first embodiment, a description will be given of an example in which the first rotational axis 101 and the axis line of the endoscope 90 are coincident.

The first gimbal portion 21 is arranged between the holder 10 and the second gimbal portion 22, and has a columnar shape. The first gimbal portion 21 comprises a first end including a bearing structure. The bearing structure supports the holder 10 to be relatively rotatable about the first rotational axis 101.

The second gimbal portion 22 is arranged between the first gimbal portion 21 and the distal portion 30, and has a substantial U-shape such that the second gimbal portion 22 opens toward the first gimbal portion 21. In an opening side of the second gimbal portion 22 (an opening side of the U-shape, hereinafter the same), the first gimbal portion 21 is arranged. A bearing structure to support the first gimbal portion 21 to be relatively rotatable about the second rotational axis 102 is provided between ends of the second gimbal portion 22 at the opening side and a circumferential surface of the first gimbal portion 21.

The distal portion 30 supports the endoscope 90 to be rotatable about a third rotational axis 103 that extends to intersect (more preferably, to be orthogonal to) a plane including the first rotational axis 101 and the second rotational axis 102. A mounting surface 31, on which the second gimbal portion 22 is mounted, in the distal portion 30 is a surface that is orthogonal to the third rotational axis 103. A bearing structure to support the second gimbal portion 22 to be relatively rotatable about the third rotational axis 103 is provided between the distal portion 30 and the second gimbal portion 22.

The mounting surface 31 is a surface of the distal portion 30 positioned distally relative to the first arm portion 40, and the surface is inclined relative to the horizontal plane or vertical plane. The third rotational axis 103 orthogonal to the mounting surface 31 has an inclination θ of 45 degrees relative to the horizontal direction.

Although a description will be given of an example in which the inclination θ of the third rotational axis 103 is 45 degrees in the first embodiment, the inclination θ of the third rotational axis 103 may be any value within a range from the horizontal direction to the vertical direction (excluding the horizontal direction and the vertical direction). Also, a reference for the inclination θ of the third rotational axis 103 may be the horizontal direction as described above or may be the vertical direction.

Figure 4:
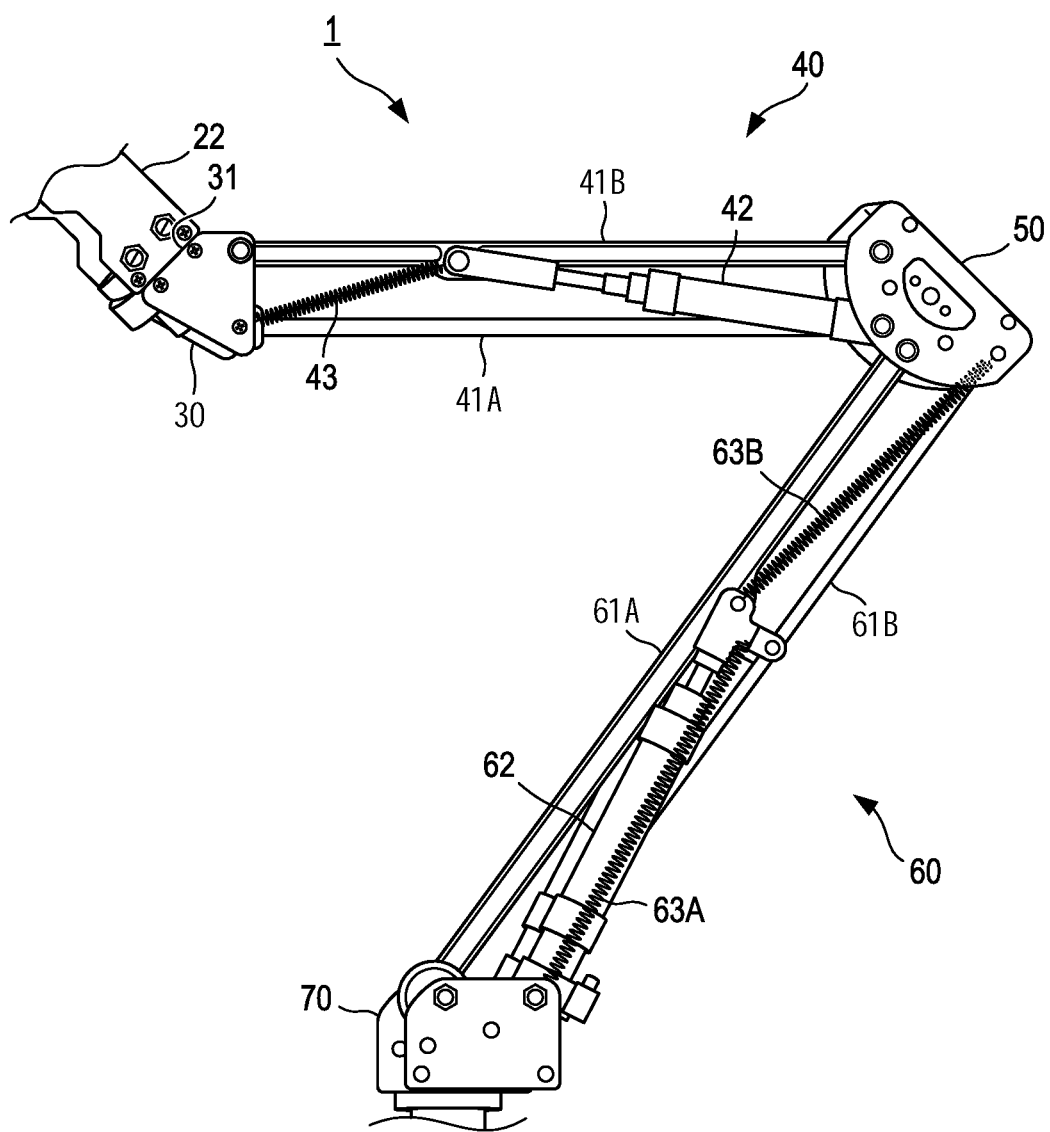
FIG. 4 is a partial enlarged view illustrating configurations of a first arm portion and a second arm portion in FIG. 1.

As shown in FIG. 4, the first arm portion 40 forms a parallel link mechanism together with the distal portion 30 and the joint 50, and allows relative movement of the distal portion 30 and the joint 50, while maintaining a relative attitude therebetween. The first arm portion 40 comprises an inner first rod 41A and an outer first rod 41B, a first air pressure actuator (an air pressure actuator) 42 and a first gravity compensator (a gravity compensator) 43.

Each of the inner first rod 41A and the outer first rod 41B is a rod-shaped member, and comprises a first end rotatably mounted on the distal portion 30 and a second end rotatably mounted on the joint 50. The inner first rod 41A and the outer first rod 41B are arranged in parallel to each other.

The first air pressure actuator 42 moves a relative position between the distal portion 30 and the joint 50. In the first embodiment, the first air pressure actuator 42 is an actuator that comprises a cylinder and a piston, and slidingly drives the piston when receiving supply of pressurized air.

The first air pressure actuator 42 comprises a second end (for example, an end on a cylinder side) that is rotatably mounted on the joint 50 at a position or its vicinity where the inner first rod 41A is mounted. The first air pressure actuator 42 comprises a second end (for example, an end on a piston side) that is rotatably mounted on an approximate middle portion of the outer first rod 41B.

A mounting position of the second end of the first air pressure actuator 42 may be at a center of the outer first rod 41B, or may be a position closer to the distal portion 30 from the center of the outer first rod 41B, or may be a position closer to the joint 50 from the center of the outer first rod 41B.

The first gravity compensator 43 exerts a force to move the distal portion 30 upward. The first gravity compensator 43 may be a tension spring. The first gravity compensator 43 comprises a first end that is mounted on the distal portion 30 at a position or its vicinity where the inner first rod 41A is mounted. The first gravity compensator 43 comprises a second end that is mounted on an approximate middle portion of the outer first rod 41B. In the first embodiment, the second end of the first gravity compensator 43 is mounted on the outer first rod 41B at the mounting position, or its vicinity, of the second end of the first air pressure actuator 42.

A second arm portion 60 forms, together with the joint 50 and the base 70, a parallel link mechanism, and allows relative movement of the joint 50 and the base 70, while maintaining a relative attitude therebetween. The second arm portion 60 comprises an inner second rod 61A and an outer second rod 61B, a second air pressure actuator (an air pressure actuator) 62, and a lower second gravity compensator (a gravity compensator) 63A and an upper second gravity compensator (a gravity compensator) 63B.

Each of the inner second rod 61A and the outer second rod 61B is a rod-shaped member, and comprises a first end rotatably mounted on the joint 50 and a second end rotatably mounted on the base 70. The inner second rod 61A and the outer second rod 61B are arranged in parallel to each other.

The second air pressure actuator 62 moves a relative position between the joint 50 and the base 70. In the first embodiment, the second air pressure actuator 62 is an actuator that comprises a cylinder and a piston, and slidingly drives the piston when receiving supply of pressurized air.

The second air pressure actuator 62 comprises a first end (for example, a cylinder side end) that is rotatably mounted on the base 70 at a position or its vicinity where the outer second rod 61B is mounted. The second air pressure actuator 62 comprises a second end (for example, a piston side end) that is rotatably mounted on an approximate middle portion of the inner second rod 61A.

A mounting position of the second end of the second air pressure actuator 62 may be at a center of the inner second rod 61A, or may be a position closer to the joint 50 from the center of the inner second rod 61A, or may be a position closer to the base 70 from the center of the inner second rod 61A.

The lower second gravity compensator 63A and the upper second gravity compensator 63B exerts a force to move the second arm portion 60 along the vertical direction. The lower second gravity compensator 63A and the upper second gravity compensator 63B each may be a tension spring. The lower second gravity compensator 63A comprises a first end that is mounted on the base 70 at a position or its vicinity where the outer second rod 61B is mounted. The second gravity compensator 63A comprises a second end that is mounted on an approximate middle portion of the inner second rod 61. The second end of the second gravity compensator 63A is mounted at the mounting position or its vicinity of the second end of the second air pressure actuator 62. The upper second gravity compensator 63B comprises a first end that is mounted on the joint 50 at a position or its vicinity where the outer second rod 61B is mounted. The upper second gravity compensator 63B comprises a second end that is mounted on an approximate middle portion of the inner second rod 61A.

The holding portion 80 is attachable to and detachable from a place (for example, a bed to be used during endoscopic surgery) at which the endoscope 90 is to be arranged for use. The holding portion 80 is arranged adjacent to the base 70, and supports the base 70 in a relatively rotatable manner about a fourth rotational axis 104 (see FIG. 2) extending along the vertical direction. An attachment and detachment structure of the holding portion 80 may be any publicly-known one, and is not limited to any particular structure.

A description will next be given of a movement of the arm device 1. First, a movement of the gimbal mechanism 20 will be described with reference to FIG. 2 and FIG. 3.

When the second gimbal portion 22 rotates relative to the distal portion 30 about the third rotational axis 103, the first gimbal portion 21, the holder 10, and the endoscope 90 also rotate, together with the second gimbal portion 22, about the third rotational axis 103. When the first gimbal portion 21 rotates relative to the second gimbal portion 22 about the second rotational axis 102, the holder 10 and the endoscope 90 also rotate, together with the first gimbal portion 21, about the second rotational axis 102.

When the holder 10 rotates relative to the first gimbal portion 21 about the first rotational axis 101, the endoscope 90 also rotates, together with the holder 10, about the first rotational axis 101. Accordingly, the endoscope 90 is movable along rotational directions about three axes, i.e., the first rotational axis 101, the second rotational axis 102, and the third rotational axis 103.

Next, a description will be given of a movement of the distal portion 30 relative to the base 70, in other words, movements of the first arm portion 40 and the second arm portion 60 with reference to FIG. 2 and FIG. 4.

First described are the movements of the first arm portion 40 and the second arm portion 60 by the first air pressure actuator 42 and the second air pressure actuator 62, and next described are the movements of the first arm portion 40 and the second arm portion 60 by the first gravity compensator 43, and by the lower second gravity compensator 63A and the upper second gravity compensator 63B.

The second air pressure actuator 62 drives the piston when receiving supply of pressurized air for driving. For example, when the piston projects from the cylinder, a longitudinal dimension of the second air pressure actuator 62 will be increased. Then, the inner second rod 61A and the outer second rod 61B of the second arm portion 60 rotate toward a direction of approaching the vertical direction. In other words, the rotation is such that the joint 50 moves upward. In reverse, when the piston withdraws into the cylinder, the longitudinal dimension of the second air pressure actuator 62 will be decreased. Thus, the inner second rod 61A and the outer second rod 61B of the second arm portion 60 rotate toward a direction of approaching the horizontal direction. In other words, the rotation is such that the joint 50 moves downward.

In the first air pressure actuator 42, similarly to the second air pressure actuator 62, the piston projects from or withdraws into the cylinder by supply of pressurized air for driving. When a longitudinal dimension of the first air pressure actuator 42 is increased, the inner first rod 41A and the outer first rod 41B of the first arm portion 40 rotate such that the distal portion 30 moves upward. In reverse, when the longitudinal dimension of the first air pressure actuator 42 is decreased, the inner first rod 41A and the outer first rod 41B of the first arm portion 40 rotate such that the distal portion 30 moves downward.

The lower second gravity compensator 63A and the upper second gravity compensator 63B are each mounted on the second arm portion 60 in a stretched state to have an increased longitudinal dimension. Thus, each of the lower second gravity compensator 63A and the upper second gravity compensator 63B generates a biasing force along a direction of shortening its longitudinal dimension. The biasing forces serve as forces to cause the joint 50 to rotate upward against the gravity of the endoscope 90 and other components.

The first gravity compensator 43 is mounted on the first arm portion 40 in a stretched state to have an increased longitudinal dimension. Thus, the first gravity compensator 43 generates a biasing force along a direction of shortening its longitudinal dimension. The biasing force serves as a force to cause the distal portion 30 to rotate upward against the gravity of the endoscope 90 and other components.

According to the arm device 1 configured as described above, the inclination θ of the third rotational axis 103 is 45 degrees, which is greater than 0 degree and smaller than 90 degrees, and thus the first rotational axis 101 and the third rotational axis 103 will not have the same inclination angle during endoscopic surgery. In other words, degrees of freedom of rotation of the endoscope 90 to be supported will not be reduced from three to two.

Figure 5:
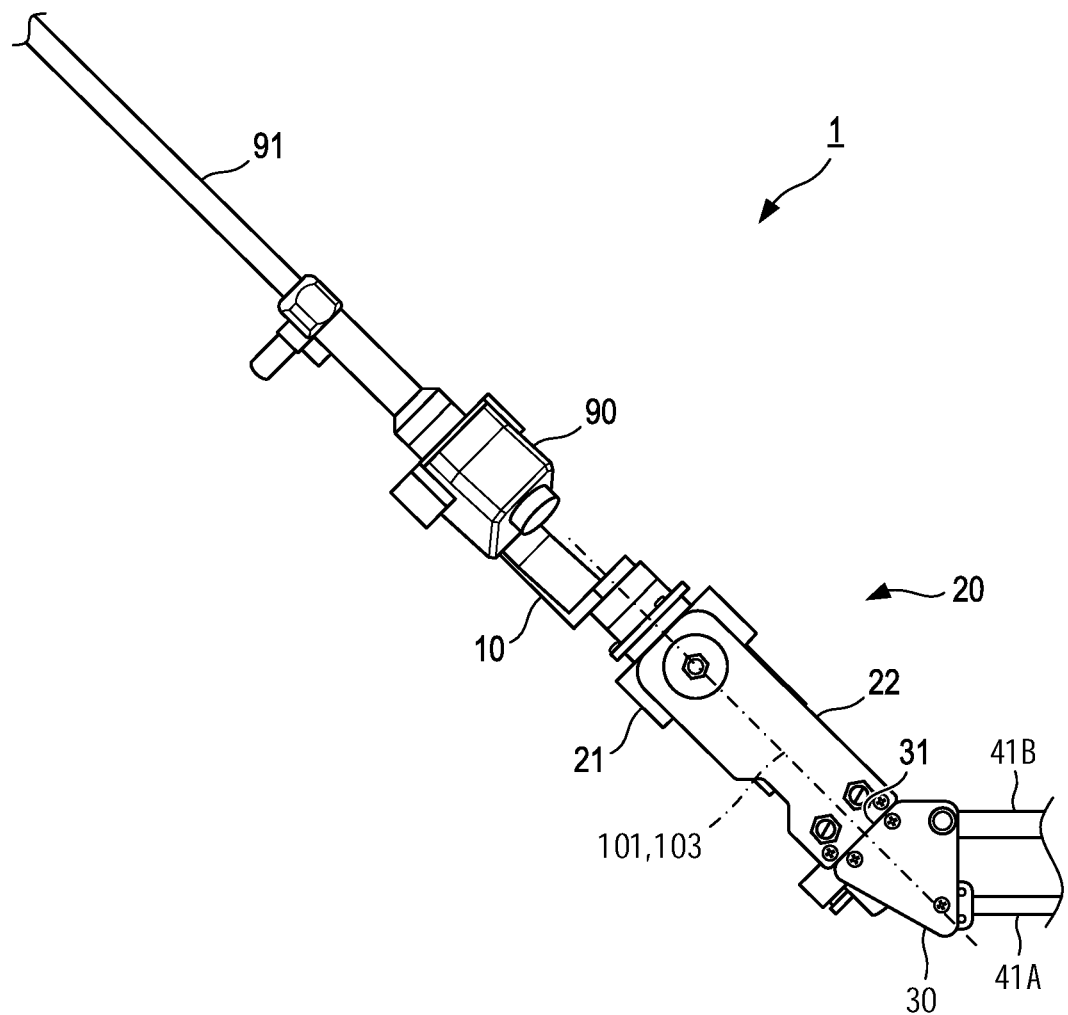
FIG. 5 is a partial enlarged view illustrating an attitude in which a first rotational axis and a third rotational axis of the arm device have a same inclination angle.

Specifically, an attitude of the arm device 1 in which the first rotational axis 101 and the third rotational axis 103 have the same inclination angle is an attitude in which the endoscope 90 extends obliquely upward, as shown in FIG. 5. During endoscopic surgery, the endoscope 90 is not used in the attitude shown in FIG. 5, and thus degrees of freedom of rotation of the endoscope 90 to be supported will not be reduced from three to two.

Figure 6A:
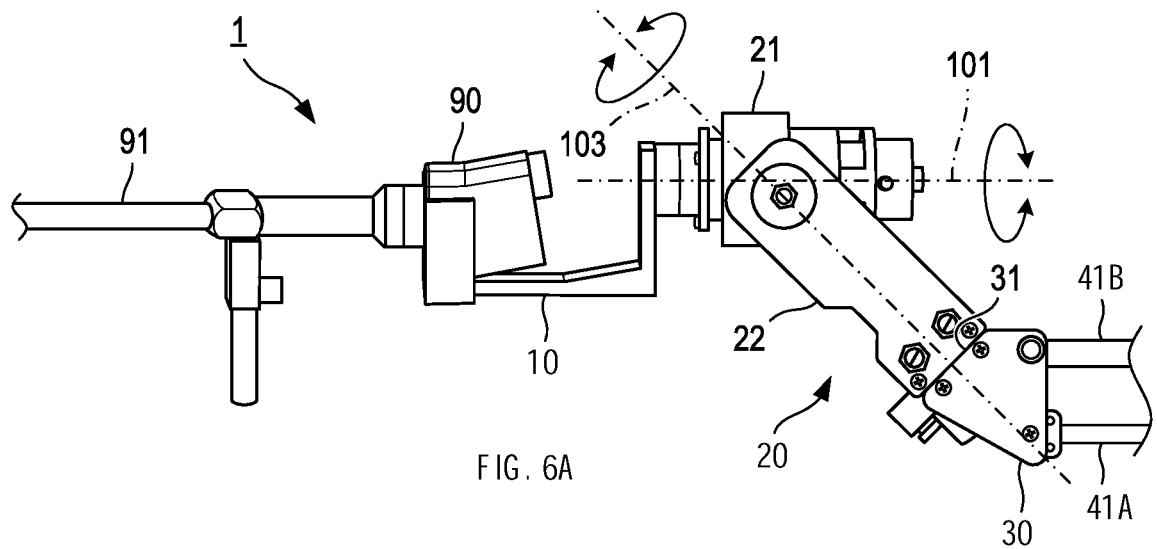
FIG. 6A is a partial enlarged view illustrating an attitude of the arm device when an axis line of an endoscope is oriented horizontal.
Figure 6B:
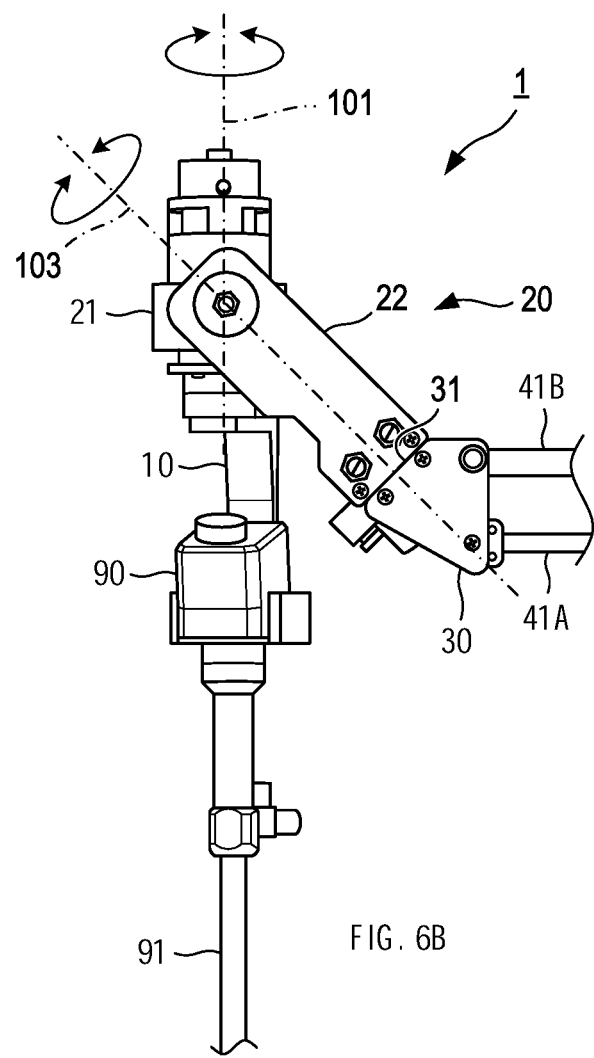
FIG. 6B is a partial enlarged view illustrating an attitude of the arm device when the axis line of the endoscope is oriented vertical.

By specifying the inclination angle of the third rotational axis 103 as 45 degrees, symmetric operation of the arm device 1 is achieved when the axis line of the endoscope 90 is oriented horizontal (see FIG. 6A) and when the axis line of the endoscope 90 is oriented vertical (see FIG. 6B). Thus, an operation angle range of the endoscope 90 can be substantially maximum.

Supporting the distal portion 30 by the first arm portion 40 and the second arm portion 60 each having a parallel link facilitates retaining the attitude of the distal portion 30 irrespective of change of an arrangement position of the distal portion 30. In other words, the inclination angle of the third rotational axis 103 can be easily maintained constant.

By providing the first gravity compensator 43, and the lower second gravity compensator 63A and the upper second gravity compensator 63B, as compared with a case where no gravity compensator is provided, it is possible to reduce a driving force required for the first air pressure actuator 42 and the second air pressure actuator 62 to move the position of the distal portion 30 supporting the endoscope 90. Thus, size reduction of the first air pressure actuator 42 and the second air pressure actuator 62 can be further facilitated.

For example, as compared with a counter-weight arm device provided with a counter weight that balances with a weight of the distal portion 30 supporting the endoscope 90, size reduction of a rear part of the arm device 1 located opposite to the extending direction of the endoscope 90 can be facilitated. Such size reduction of the rear part reduces interference by the arm device 1 of operation by an operator, an assistant, or a nurse during endoscopic surgery.

Use of the first air pressure actuator 42 and the second air pressure actuator 62 facilitates an increase in power-to-weight ratio, and allows achievement of simplified linear motion without using a deceleration mechanism. Accordingly, size reduction of the arm device 1 can be facilitated.

By providing the holding portion 80, fixation of the arm device 1 to a specified place can be facilitated. For example, fixation of the arm device 1 to a surgical bed in endoscopic surgery is facilitated, and thus it can be facilitated to maintain the attitude of the distal portion 30 constant when an operation, such as tilting the surgical bed for postural change of a patient, is performed.

Second Embodiment

Next, a second embodiment will be described with reference to FIG. 7. An arm device of the second embodiment has a similar basic configuration to that of the first embodiment, but is different from the first embodiment in respective configurations of the first arm portion and the second arm portion. Thus, in the second embodiment, the configurations of the first arm portion and the second arm portion will be described using FIG. 7, and no further description will be given of other elements.

Figure 7:
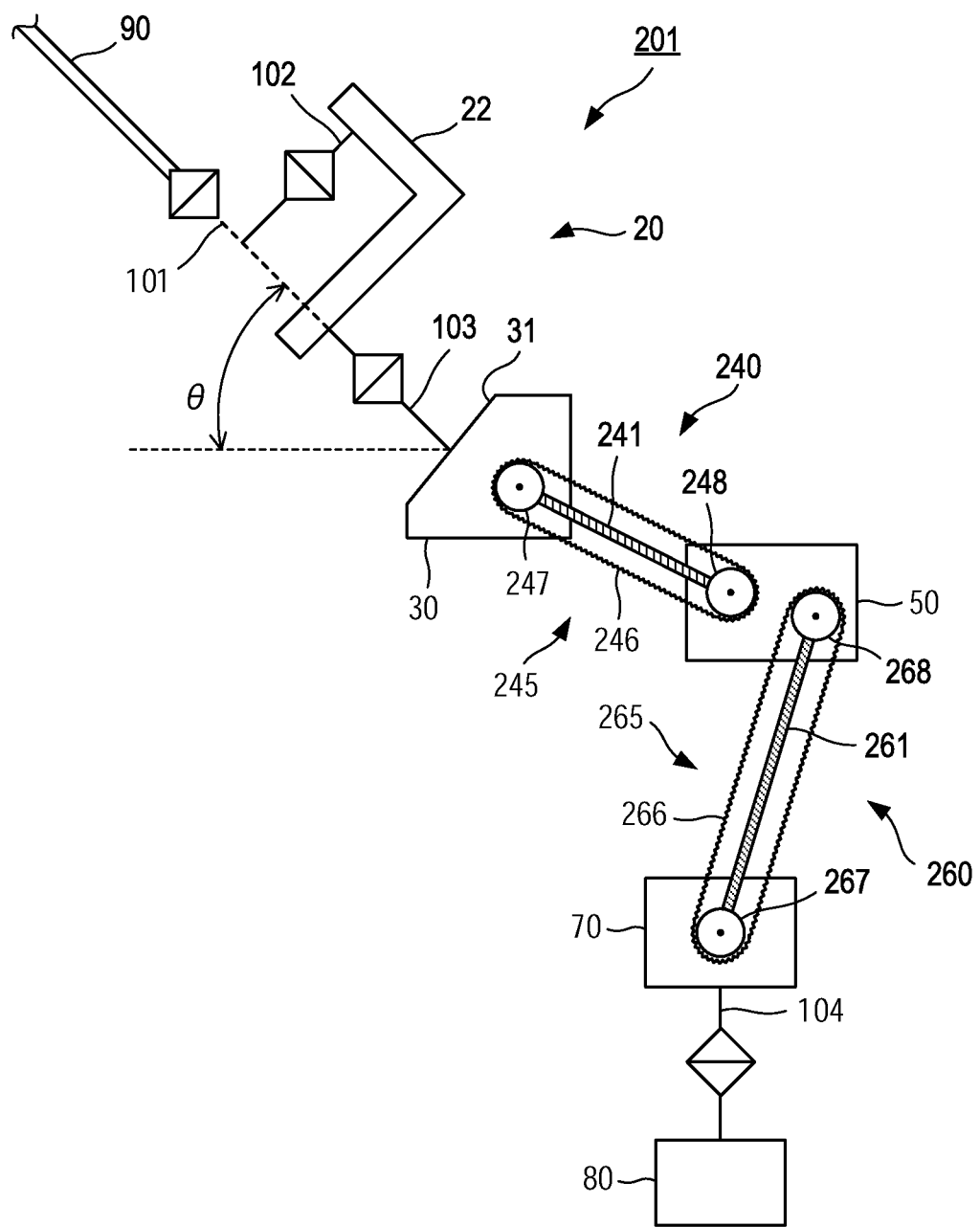
FIG. 7 is a schematic diagram illustrating a configuration of an arm device of a second embodiment.

As shown in FIG. 7, a first arm portion 240 in an arm device 201 of the second embodiment forms, together with the distal portion 30 and the joint 50, a belt connecting arm mechanism, and allows relative movement of the distal portion 30 and the joint 50, while maintaining a relative attitude therebetween. The first arm portion 240 comprises a first link portion (a link portion) 241 and a first drive portion (a drive portion) 245.

The first link portion 241 is a rod-shaped member having a first end rotatably mounted on the distal portion 30 and a second end rotatably mounted on the joint 50. In the second embodiment, the first link portion 241 is provided singly.

The first drive portion 245 causes a relative movement of the distal portion 30 and the joint 50 while maintaining a relative attitude of the distal portion 30 and the joint 50. The first drive portion 245 comprises a first belt 246, a distal-portion-side gear 247 and a first-joint-side gear 248.

The first belt 246 is an annular-shaped member, and is arranged to be wound around the distal-portion-side gear 247 and the first-joint-side gear 248. Also, the first belt 246 comprises an engagement configuration to engage with the distal-portion-side gear 247 and the first-joint-side gear 248.

The distal-portion-side gear 247 is a disk-shaped or column-shaped member arranged in the distal portion 30a, and comprises a circumferential surface around which the first belt 246 is wound and an engagement configuration formed along the circumferential surface to engage with the first belt 246.

The first-joint-side gear 248 is a disk-shaped or column-shaped member arranged in the joint 50, and comprises a circumferential surface around which the first belt 246 is wound and an engagement configuration formed along the circumferential surface to engage with the first belt 246.

The second arm portion 260 forms, together with the joint 50 and the base 70, a belt connecting arm mechanism, and allows relative movement of the joint 50 and the base 70, while maintaining a relative attitude therebetween. The second arm portion 260 comprises a second link portion (a link portion) 261 and a second drive portion (a drive portion) 265.

The second link portion 261 is a rod-shaped member having a first end rotatably mounted on the joint 50 and a second end rotatably mounted on the base 70. In the second embodiment, the second link portion 261 is provided singly.

The second drive portion 265 causes a relative movement of the joint 50 and the base 70 while maintaining a relative attitude of the joint 50 and the base 70. The second drive portion 265 comprises a second belt 266, a base-side gear 267, and a second-joint-side gear 268.

The second belt 266 is an annular-shaped member, and is arranged to be wound around the base-side gear 267 and the second-joint-side gear 268. Also, the second belt 266 comprises an engagement configuration to engage with the base-side gear 267 and the second-joint-side gear 268.

The base-side gear 267 is a disk-shaped or column-shaped member arranged in the base 70, and comprises a circumferential surface along which the second belt 266 is wound and an engagement configuration formed along the circumferential surface to engage with the second belt 266.

The second-joint-side gear 268 is a disk-shaped or column-shaped member arranged in the joint 50, and comprises a circumferential surface around which the second belt 266 is wound and an engagement configuration formed along the circumferential surface to engage with the second belt 266.

Next, a description will be given of a movement of the arm device 201, specifically a movement of the distal portion 30 relative to the base 70, and in other words, movements of the first arm portion 40 and the second arm portion 60. The movement of the gimbal mechanism 20 is similar to that in the first embodiment, and accordingly will not be further described.

In case of relative movement of the joint 50 with respect to the base 70, the joint 50 makes the relative movement while being supported by the second link portion 261. Specifically, the second link portion 261 changes its relative attitude (inclination) while making a relative rotation with respect to the base 70 and the joint 50.

The relative attitude of the joint 50 with respect to the base 70 is maintained constant as described below. Specifically, the second belt 266 is driven in accordance with the change in the relative attitude of the joint 50 caused by the relative movement. Driving of the second belt 266 causes a rotational driving of the second-joint-side gear 268, and the relative attitude of the joint 50 is maintained constant by the rotational driving.

The relative attitude of the joint 50 may be maintained constant, for example, by rotating the base-side gear 267 using an electric motor, such as a motor, to thereby drive the second belt 266 and rotationally drive the second-joint-side gear 268 fixed to the joint 50. Alternatively, the relative attitude of the joint 50 may be maintained constant by fixing the base-side gear 267 to the base 70 and driving the second belt 266 through relative movement of the joint 50 and the fixed base-side gear 267, to thereby transmit rotation of the second-joint-side gear 268 by the driving of the second belt 266 through a gear or the like to the joint 50. A method for maintaining the relative attitude of the joint 50 constant may be any publicly-known method, and is not limited to any particular one.

In case of relative movement of the distal portion 30 with respect to the joint 50, the distal portion 30 makes the relative movement while being supported by the first link portion 241. Specifically, the first link portion 241 changes its relative attitude (inclination) while making a relative rotation with respect to the joint 50 and the distal portion 30.

The relative attitude of the distal portion 30 with respect to the joint 50 is maintained constant as described below. Specifically, the first belt 246 is driven in accordance with the change in the relative attitude of the distal portion 30 caused by the relative movement. Driving of the first belt 246 causes a rotational driving of the first-joint-side gear 248, and the relative attitude of the distal portion 30 is maintained constant by the rotational driving.

The relative attitude of the distal portion 30 may be maintained constant, for example, by rotating the first-joint-side gear 248 using an electric motor, such as a motor, to thereby drive the first belt 246 and rotationally drive the distal-portion-side gear 247 fixed to the distal portion 30. Alternatively, the relative attitude of the distal portion 30 may be maintained constant by fixing the first-joint-side gear 248 to the joint 50 and driving the first belt 246 through relative movement of the distal portion 30 and the fixed first-joint-side gear 248, to thereby transmit rotation of the distal-portion-side gear 247 by the driving of the first belt 246 through a gear or the like to the distal portion 30. A method for maintaining the relative attitude of the distal portion 30 constant may be any publicly-known method, and is not limited to any particular one.

According to the arm device 201 with the aforementioned configuration, the first link portion 241 and the first drive portion 245, as well as the second link portion 261 and the second drive portion 265 support the distal portion 30, thereby facilitating maintaining the attitude of the distal portion 30 constant even when the arrangement position of the distal portion 30 is changed. In other words, the inclination angle of the third rotational axis 103 can be easily maintained constant.

Although the first belt 246 is provided to the first drive portion 245, and the second belt 266 is provided to the first belt 246 in the second embodiment, a member using a wire may be employed in place of the first belt 246 and the second belt 266.

Third Embodiment

Next, a third embodiment will be described with reference to FIG. 8. An arm device of the third embodiment has a similar basic configuration to that of the first embodiment, but is different from the first embodiment in configurations of the first arm portion and the second arm portion. Thus, in the third embodiment, respective configurations of the first arm portion and the second arm portion will be described using FIG. 8, and no description will be given of other elements.

Figure 8:
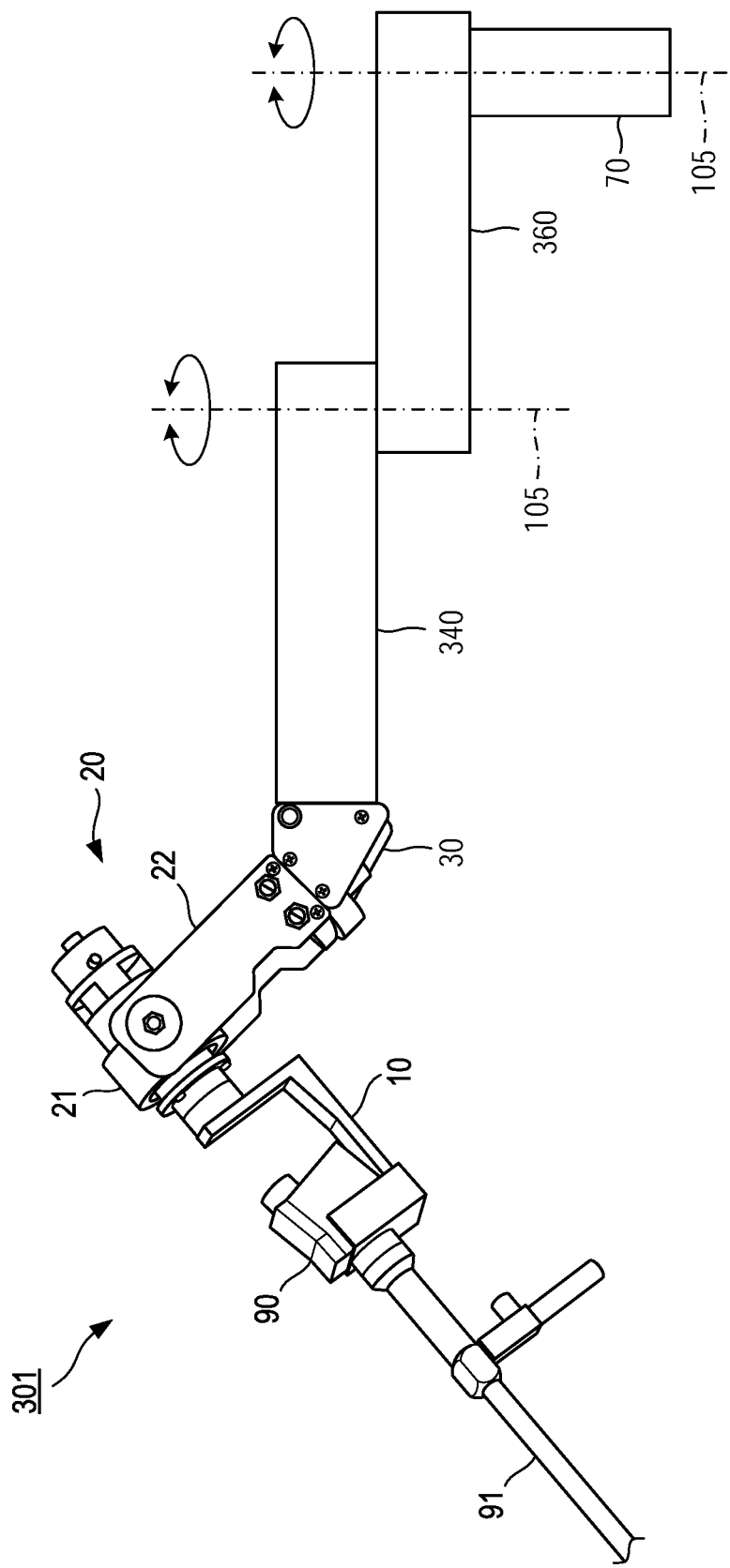
FIG. 8 is a view illustrating a configuration of an arm device of a third embodiment.

As shown in FIG. 8, an arm device 301 of the third embodiment comprises the holder 10, the gimbal mechanism 20, the distal portion 30, a first arm portion (an arm portion) 340, a second arm portion (an arm portion) 360, and the base 70.

The first arm portion 340 is a columnar member arranged between the distal portion 30 and the second arm portion 360 and extending laterally or horizontally. Although the first arm portion 340 extends horizontally in the third embodiment, the first arm portion 340 may have an end at a distal portion 30 side inclined upward or downward toward the distal portion 30.

The second arm portion 360 is a columnar member arranged between the first arm portion 340 and the base 70 and extending laterally or horizontally. Although the second arm portion 360 extends horizontally in the third embodiment, the second arm portion 360 may have an end at a base 70 side inclined upward or downward toward the base 70.

The first arm portion 340 and the second arm portion 360 are arranged to overlap each other such that an end of the first arm portion 340 is positioned above and an end of the second arm portion 360 is positioned below. Provided between the first arm portion 340 and the second arm portion 360 is a bearing structure to allow their relative rotation about a first arm rotational axis (a rotational axis line) 105 extending vertically.

The second arm portion 360 and the base 70 are arranged such that an end of the second arm portion 360 overlaps an upper end of the base 70. Provided between the second arm portion 360 and the base 70 is a bearing structure to allow their relative rotation about a second arm rotational axis (a rotational axis line) 106 extending vertically.

According to the arm device 301 configured as described above, the first arm portion 340 that extends along the horizontal direction and is configured to rotate about the first arm rotational axis (the rotational axis line) 105 extending vertically, and the second arm portion 360 that extends along the horizontal direction and is configured to rotate about the second arm rotational axis 106 extending vertically support the distal portion 30, thereby facilitating maintaining the attitude of the distal portion 30 constant even when the arrangement position of the distal portion 30 is changed.

Fourth Embodiment

Figure 9:
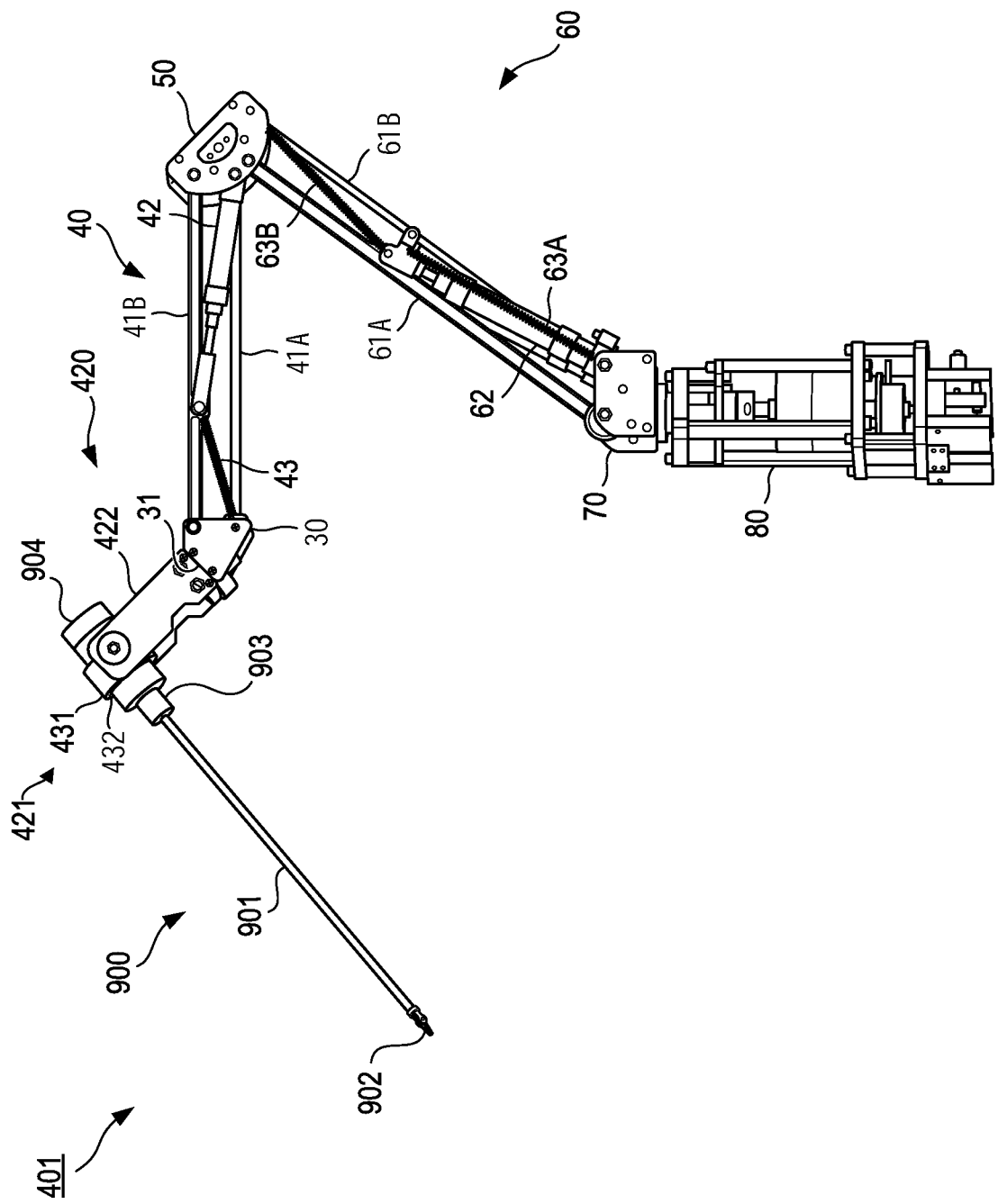
FIG. 9 is a view illustrating a configuration of an arm device of a fourth embodiment.

Next, a fourth embodiment will be described with reference to FIG. 9. An arm device of the fourth embodiment has a similar basic configuration to that of the first embodiment, but is different from the first embodiment in type of an instrument to be held by an arm device 401, and a configuration of a gimbal mechanism. Thus, in the fourth embodiment, a description will be given mainly of a configuration related to the instrument to be held by the arm device 401 and the gimbal mechanism, and no description will be given of other elements.

The arm device 401 of the fourth embodiment holds a robot forceps 900. As shown in FIG. 9, the arm device 401 comprises a gimbal mechanism 420, the distal portion 30, the first arm portion (the arm portion) 40, the joint 50, the second arm portion (the arm portion) 60, the base 70, and the holding portion 80.

The gimbal mechanism 420 comprises a first gimbal portion 421 and a second gimbal portion 422. The first gimbal portion 421 holds the robot forceps 900 so as to be rotatable about the first rotational axis 101 extending along an axis line of a shaft 901 of the robot forceps 900. The second gimbal portion 422 holds the robot forceps 900 so as to be rotatable about the second rotational axis 102 extending along an intersecting direction (more preferably an orthogonal direction) with the first rotational axis 101.

The robot forceps 900 held by the arm device 401 is an instrument that is inserted into a body cavity of a patient, for example, in endoscopic surgery, to grasp a tissue of an affected area through a remote operation by a user. The robot forceps 900 comprises an elongated rod-shaped shaft 901, a forceps portion 902 provided at a distal end of the shaft 901, a cartridge 903 provided at a proximal end of the shaft 901, and a driver 904 to which the cartridge 903 is connected.

The driver 904 is a drive portion to transmit power to the cartridge 903. The driver 904 is connected to a not-shown controller, and transmits a specified power to the cartridge 903 in accordance with a control signal from a controller based on, for example, a user's operation. The driver 904 comprises a not-shown fixation mechanism to detachably fix the cartridge 903, and the cartridge 903 described below is detachably fixed thereto.

The cartridge 903 is a mechanism to drive the forceps portion 902 with the power transmitted from the driver 904. The shaft 901 extends from a surface of the cartridge 903 opposite to the driver 904 in an extending direction of the first rotational axis 101.

The shaft 901 is a cylindrical rod-shaped member and transmits the power inputted from the cartridge 903 to the forceps portion 902. Specifically, the power inputted from the cartridge 903 is transmitted to the forceps portion 902 through a not-shown power transmission member, such as a wire, provided inside the shaft 901. The cartridge 903 may comprise a shaft rotation mechanism to relatively rotate the shaft 901 with respect to the cartridge 903 about the axis line of the shaft 901. In this case, the cartridge 903 rotates the shaft 901 in a specified direction about the axis line of the shaft 901 with the driving force transmitted from the driver 904. The axis line of the shaft 901 here is a center axis line passing through the center of any cross section of the shaft 901. The shaft 901 may be attachable to and detachable from the cartridge 903.

The forceps portion 902 performs an opening/closing action by the driving force transmitted through the shaft 901, to thereby grasp a tissue or the like. A part of the forceps portion 902 to grasp a tissue or the like may have a function as an electric scalpel for, for example, tissue dissection and hemostasis. The configuration of the robot forceps 900 shown in FIG. 9 is an example, and any other configuration that is suitable to be held by the arm device 401 may be employed.

The first gimbal portion 421 forming the gimbal mechanism 420 of the fourth embodiment comprises a rotation mechanism to hold the robot forceps 900 to be rotatable about the first rotational axis 101 at a position where the axis line of the shaft 901 and the first rotational axis 101 are coincident.

In the fourth embodiment, the first gimbal portion 421 has a cylindrical shape with a larger inner diameter than the driver 904 and is configured to rotatably hold the driver 904 inserted in the cylindrical shape. Specifically, the first gimbal portion 421 comprises an outer cylinder portion 431, an inner cylinder portion 432 having a cylindrical shape and arranged inside the outer cylinder portion 431, a not-shown inner cylinder support, and a not-shown driver holder.

The outer cylinder portion 431 has a cylindrical shape with a larger inner diameter that an outer diameter of the driver 904 and is supported by the second gimbal portion 422 rotatably about the second rotational axis 102. The inner cylinder portion 432 has a cylindrical shape with a smaller outer diameter than an inner diameter of the outer cylinder portion 431 and a larger inner diameter than the driver 904, and is arranged inside the outer cylinder portion 431. The inner cylinder support is arranged between the outer cylinder portion 431 and the inner cylinder portion 432, and supports the inner cylinder portion 432 arranged inside the outer cylinder portion 431 so as to be relatively rotatable with respect to the outer cylinder portion 431 at a position where a center axis line of the inner cylinder portion 432 and a center axis line of the outer cylinder portion 431 are coincident. The inner cylinder support may be a bearing. In the fourth embodiment, the center axis lines of the outer cylinder portion 431 and the inner cylinder portion 432 correspond to the first rotational axis 101. Specifically, the inner cylinder portion 432 is supported relatively rotatably with respect to the outer cylinder portion 431 about the same center axis line (the first rotational axis 101) as the outer cylinder portion 431.

An inner side surface of the inner cylinder portion 432 comprises the not-shown driver holder to secure the inserted driver 904 inside the inner cylinder portion 432. Specifically, the driver 904 held by the driver holder is relatively rotatable together with the inner cylinder portion 432 with respect to the outer cylinder portion 431. The driver holder holds the driver 904 such that the axis line of the shaft 901 and the first rotational axis 101 are coincident at any rotational position of the inner cylinder portion 432.

The first gimbal portion 421 of the fourth embodiment configured as described above can hold the robot forceps 900 rotatably about the first rotational axis 101 at the position where the axis line of the shaft 901 and the first rotational axis 101 are coincident.

The configuration of the first gimbal portion 421 is not limited to the above-described configuration, but may be any other configuration that comprises a rotation mechanism having a similar function as that of the above-described configuration.

The second gimbal portion 422 is arranged between the first gimbal portion 421 and the distal portion 30, and has similar configuration and function as the second gimbal portion 22 of the first embodiment.

Although the driver holder of the first gimbal portion 421 detachably holds the driver 904 by a publicly-known method in the fourth embodiment, the driver 904 and the first gimbal portion 421 may be, for example, integrally formed such that the shaft 901 is rotatable about the first rotational axis 101 with respect to the driver 904. Also, when the shaft 901 is attachable to and detachable from the cartridge 903 as described above, the first gimbal portion 421, the cartridge 903, and the driver 904 may be formed integrally. Further, when the cartridge 903 comprises a shaft rotation mechanism, the first gimbal portion 421 is not required to include a rotation mechanism.

According to the arm device 401 of the fourth embodiment, the first gimbal portion 421 holds the robot forceps 900 such that the axis line of the shaft 901 and the first rotational axis 101 are coincident. As a result, if the robot forceps 900 is rotated about the first rotational axis 101, for example, to change an orientation of the forceps portion 902 to grasp a tissue or the like, a position of the forceps portion 902 relative to the target tissue to grasp will not be moved, which allows a user to operate the robot forceps 900 easily. When the cartridge 903 comprises a shaft rotation mechanism, the user may drive the shaft rotation mechanism of the cartridge 903, to thereby change the orientation of the forceps portion 902. In this case, the shaft rotation mechanism of the cartridge 903 serves the function of a first gimbal portion in the appended claims.

Modified Example of Fourth Embodiment

Figure 10:
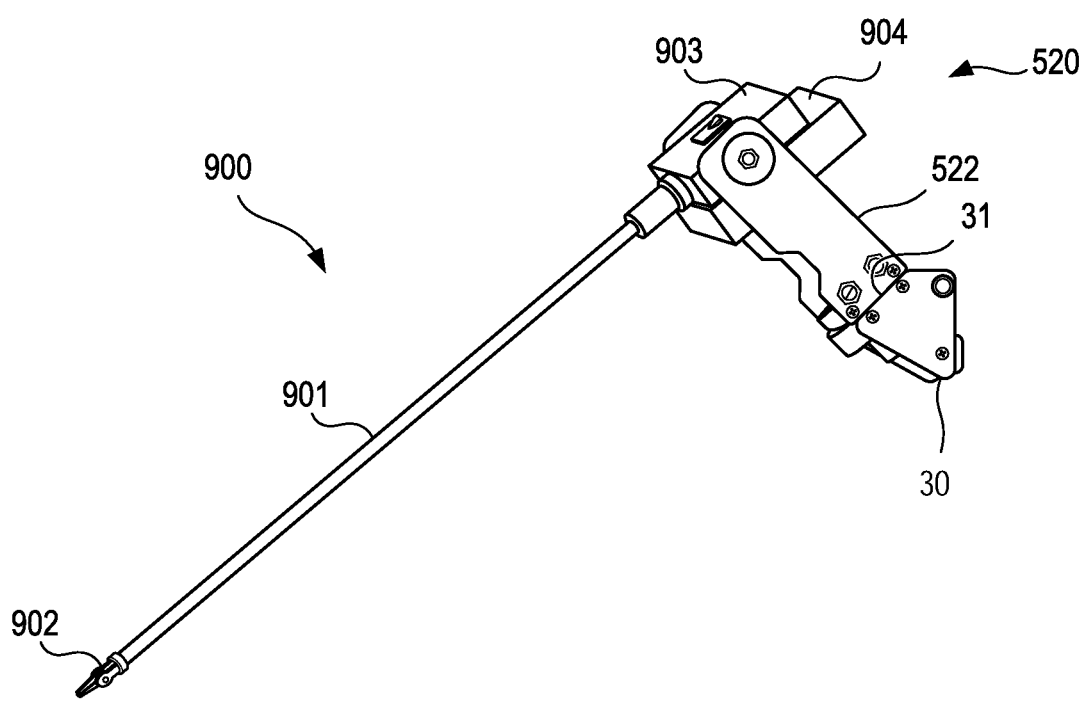
FIG. 10 is a view illustrating a configuration of an arm device of a modified example of the fourth embodiment.

When the cartridge 903 comprises the above-described shaft rotation mechanism, the second gimbal portion may be configured to directly hold the robot forceps. Hereinafter, a specific description will be given of a gimbal mechanism 520 of this modified example with reference to FIG. 10.

A second gimbal portion 522 of the gimbal mechanism 520 comprises a not-shown forceps holder to hold the robot forceps 900 rotatably about the second rotational axis 102 provided at an end opposite to the mounting surface 31. The forceps holder rotatably holds the cartridge 903 or the driver 904 about the second rotational axis 102, for example, by pinching in accordance with a user's operation. The forceps holder may rotatably hold the cartridge 903 or the driver 904 by another publicly-known method. In the modified example, the forceps holder holds the cartridge 903 or the driver 904 at a position where the axis line of the shaft 901 intersects the second rotational axis 102. Alternatively, the forceps holder may hold the cartridge 903 or the driver 904 in a positional relationship where the axis line of the shaft 901 does not intersect the second rotational axis 102.

In the modified example, in order to change a grasping orientation of the forceps portion 902, a user actuates the shaft rotation mechanism of the cartridge 903 to rotate the shaft 901, to thereby change the orientation of the forceps portion 902. In this case, the shaft rotation mechanism of the cartridge 903 serves the function of the first gimbal portion in the appended claims.

The gimbal mechanism 520 configured as described above can provide an arm device with a simple configuration.

The technical scope of the present disclosure is not limited to the above-described embodiments, but may be modified variously within a range without departing from the subject matter of the present disclosure. For example, in the above-described embodiments, descriptions have been given regarding examples in which the rotation of the second gimbal portion 22 about the third rotational axis 103, the rotation of the first gimbal portion 21 about the second rotational axis 102, the rotation of the holder 10 about the first rotational axis 101, the rotation of the first gimbal portion 421 about the first rotational axis 101, or the rotation of the robot forceps 900 about the second rotational axis 102 is preformed manually. However, such rotation operations may be performed by actuator driving. Specifically, it may be configured such that a rotation drive portion, such as a motor, is provided to a portion corresponding to each of the rotations, and the rotation drive portion is caused to drive in accordance with an external control signal, to thereby achieve a corresponding rotation operation. Also, the rotation operations each may be changed between manual operation and actuator driving, for example, depending on an intended purpose, a state of use, or by a user's selection operation. Further, the rotation operations may be configured to be performed by both of manual operation and actuator driving Moreover, the above-described embodiments may be appropriately combined.

The invention claimed is:
1. An arm device comprising:
a first gimbal portion configured to rotatably support an instrument about a first rotational axis extending along an axis line of the instrument;
a second gimbal portion configured to rotate the instrument about a second rotational axis extending along a direction intersecting the first rotational axis; and
a distal portion configured to rotate the instrument about a third rotational axis extending to intersect a plane including the first rotational axis and the second rotational axis; and
a first actuator coupled between the joint and the outer rod;
a first gravity compensator configured to apply a force to move the distal portion upward;
wherein the distal portion is coupled to at least one arm portion that includes an inner rod and an outer rod arranged parallel to the inner rod, wherein the at least one arm portion extends between the distal portion and a joint, wherein the inner rod and the outer rod are separately pivotally coupled to the distal portion to form a first parallel link mechanism that maintains a relative attitude between the distal portion and the joint, wherein the arm device is devoid of a counter-weight configured to balance with a weight of the distal portion, wherein the third rotational axis has an inclination angle greater than 0 degree and less than 90 degrees when a horizontal direction is defined as 0 degree and an upper vertical direction is defined as 90 degrees, wherein the first actuator is configured to drive the first parallel link mechanism to thereby move a position of the distal portion, wherein the first gravity compensator comprises a first end that is mounted on the distal portion at or proximate to a position where the inner rod is mounted, and wherein the first gravity compensator comprises a second end that is mounted on the first actuator at or proximate to a position where the first actuator is coupled to the outer rod.

2. The arm device according to claim 1, wherein the third rotational axis has an inclination angle of 45 degrees.

3. The arm device according to claim 1, wherein the first actuator is an air pressure actuator configured to be driven by receiving air supply.

4. The arm device according to claim 1, wherein the at least one arm portion extends along a horizontal direction, and the distal portion is configured to rotate about a rotational axis line extending vertically.

5. The arm device according to claim 1, further comprising:

a holding portion that is attachable to and detachable from a place where the instrument is to be arranged for use, wherein the holding portion is arranged adjacent to a base and supports the base in a relatively rotatable manner about a fourth rotational axis extending along a vertical direction.

6. The arm device according to claim 1, wherein:

the at least one arm portion comprises a first arm portion forming the first parallel link mechanism, and a second arm portion forming a second parallel link mechanism;

the arm device further comprises a second actuator configured to drive the second parallel link, to thereby move a position of the distal portion; and the arm device further comprises a second gravity compensator configured to apply a force to move the distal portion upward on the second parallel link mechanism.

7. The arm device according to claim 6, further comprising:

an additional gravity compensator configured to apply a force to move the distal portion upward on the first parallel link mechanism.

8. The arm device according to claim 1, wherein the arm device is configured for endoscopic surgery in at least one of digestive surgery, respiratory surgery, or urological surgery.

* * * * *

UNITED STATES PATENT AND TRADEMARK OFFICE
CERTIFICATE OF CORRECTION

PATENT NO. : 12,285,300 B2
APPLICATION NO. : 17/042678
DATED : April 29, 2025
INVENTOR(S) : Daisuke Haraguchi et al.

Page 1 of 1

It is certified that error appears in the above-identified patent and that said Letters Patent is hereby corrected as shown below:

In the Claims

Column 18, Line 14, replace "the second parallel link" with --the second parallel link mechanism--.

Signed and Sealed this
Third Day of June, 2025

Coke Morgan Stewart
*Acting Director of the United States Patent and Trademark Office*